United States Patent [19]

Tolbert et al.

[11] 4,059,485

[45] Nov. 22, 1977

[54] ADAPTATION OF CELL LINES TO SUSPENSION CULTURE

[75] Inventors: William R. Tolbert, Manchester; Joseph Feder, University City, both of Mo.

[73] Assignee: Monsanto Company, St. Louis, Mo.

[21] Appl. No.: 738,515

[22] Filed: Nov. 3, 1976

[51] Int. Cl.² ............................................. C12K 9/00
[52] U.S. Cl. ................................................... 195/1.8
[58] Field of Search ........................................ 195/1.8

[56] References Cited

U.S. PATENT DOCUMENTS 3,850,748  11/1974  Cook et al. ...................... 195/1.8

OTHER PUBLICATIONS

Willmer–Cells & Tissues in Culture vol. 1 (1965) pp. 495–496.

Primary Examiner—Sam Rosen
Attorney, Agent, or Firm—Scott J. Meyer; John D. Uphan

[57] ABSTRACT

Densely packed cells growing rapidly in substrate-attached culture are gently released from the substrate by enzymatic treatment to form aggregates ranging from 20 $\mu$ to 500 $\mu$ in diameter. These aggregates are then transferred to fresh medium in agitated liquid suspension. The cells thereby continue to grow in aggregates whereby a normally anchorage-dependent established mammalian cell line is rapidly adapted to suspension culture.

12 Claims, No Drawings

ADAPTATION OF CELL LINES TO SUSPENSION CULTURE

BACKGROUND OF THE INVENTION

This invention relates to a method of culturing mammalian cells and, more particularly, to a method for rapidly adapting mammalian cell lines to growth in agitated liquid suspension culture.

The propagation of mammalian cells in agitated liquid suspension has been carried out in many laboratories. The earliest reported work is that of Owens et al, *Ann. N.Y. Acad. Sci.* 58, 1039-55 (1954) and Earle et al, *J. Nat. Cancer Inst.* 14,1159-71 (1954). Since that time, numerous cell lines have been adapted to suspension culture. Extensive reviews on this subject have been provided by Cherry and Hull, *J. Biochem. Microbiol. Tech. Eng.* II (3), 267-85 (1960), and by Moore and Ulrich, *J. Surg. Res.* 5 (6), 270-82 (1965).

Suspension culture of mammalian cells is desirable from the standpoint of large scale propagation of cells. This method of cell culture does not have any of the time and space limitations that are inherent with conventional monolayer growth. In the past, much attention has been given to the culture apparatus conditions and the nutrient media in attempting to develop practical suspension culture methods. Examples of these culture apparatus conditions and nutrient media are those such as disclosed by Earl et al, U.S. Pat. No. 2,990,335 and McLimans et al, U.S. Pat. No. 3,039,932, respectively. In most of the reported procedures, the cells are normally grown as a bulk suspension of discrete cells. Any transient aggregation of cells during the suspension culturing has been viewed as troublesome and conditions have been arranged to avoid or eliminate such aggregation; Cook et al, *In Vitro* 9, (5) 318-30 (1974) and U.S. Pat. No. 3,850,748.

It is also known that tumor cells can be grown as multi-cell spheroids in a non-agitated suspension of soft agar; Folkman and Hochberg, *J. Expt'l Med.* 138, 745-75 (1973). In other cases, individual tumor cells have been observed to aggregate over the surface of soft agar or to slough off the surface of soft agar and float in the medium; Costachel et al., *Z. Krebsforsch* 72, 24-31 (1969).

In contrast to these prior art methods of cell propagation in suspension culture, the present invention is concerned with the intentional employment of cell aggregates as means of rapidly adapting cell growth from substrate-attached culture to agitated liquid suspension.

BRIEF DESCRIPTION OF THE INVENTION

In accordance with the present invention, densely packed cells growing rapidly in substrate-attached culture are gently released from the substrate by enzymatic treatment to form aggregates ranging from about 20 $\mu$ (micron) to about 500 $\mu$ in diameter. These aggregates are then transferred to fresh medium in an agitated liquid suspension whereby he cells continue to grow in aggregates. It has been found that within these aggregates, cell-to-cell contacts and interactions can satisfactorily substitute for the cell-to-substrate contacts, thereby allowing liquid suspension growth of normally anchoragedependent cells. The cells continue to divide with the same doubling time as found in substrate-attached cultures with little or no adaptation period required.

The long adaptation process heretofore usually required for conversion from substrate anchorage dependance to single cell suspension culture involves selection of cells with differing properties and potential loss of the desired product. The rapid conversion to aggregate suspension as defined herein does not requre such selection and generally avoids loss of cell properties. Cells can be propagated for long periods as aggregate suspensions or can be frequently converted from substrate-attached cultures if continued suspension propagation selects against any desired properties. Also, cells can be kept frozen for long periods of time, thawed and seeded in the substrate-attached culture and rapidly converted to aggregate suspension in accordance with this invention.

DETAILED DESCRIPTION OF THE INVENTION

The desired cell line is first grown in a substrate-attached attached culture. During the substrate-attached growth peiod, the cell line should be adapted for rapid growth in the same medium that is to be subsequently used in the suspension culture.

A variety of normally anchorage-dependent established mammalian cell lines have been rapidly adapted to growth in agitated liquid suspension culture by the method of this invention. These cell lines are by way of example and illustration and not limitation of the invention as follows:

The human lung, SV-40 transformed cell line designated WI38, VA13; ATCC No. CCL 75.1.

The human lung, SV-40 transformed cell line designated WI26, VA4; ATCC No. CCL 95.1.

The mouse kidney, SV-40 transformed cell line designated TCMK-1; ATCC No. CCL 139.

The mouse renal adenocarcinoma cell line designated RAG; ATCC No. CCL 142.

The mouse embryo, Kirsten virus transformed cell line designated KNIH.

The mouse embryo, SV-40 transformed cell line designated SV3T3.

Cultures of the latter two cell lines for use in this invention were obtained from Dr. Judah Folkman of the Harvard Medical School while cultures of the others were obtained from the American Type Culture Collection, Rockland, Maryland. The SV3T3 cell line also is further described in the copending application Ser. No. 738,513, filed simultaneously herewith, and assigned to a common assignee. The KNIH cell line is derived from NIH mouse embryo fibroblasts, originally cultured by Jainchill et al, *J. Virology* 4, 549-53 (1969), which have been transformed by Kirsten virus, a murine sarcoma virus isolated by Kirsten et al, *J. Nat. Cancer Inst.* 39, 311-35 (1967).

Other suitable established cell lines for adaption to agitated liquid suspension culture according to the method of this invention will be apparent to the person skilled in the art. For purposes of this invention, by the term "established" cell line is meant a cell line which demonstrates the potential to be subcultured indefinitely in vitro. This is in accordance with the proposed usage of animal tissue culture terms by S. Federoff accepted by the Tissue Culture Association at its Annual Meeting on June 3, 1966 in San Francisco.

Suitable culture media for the cell growth will contain assimilable sources of nitrogen, carbon and inorganic salts. These can be any of the well-known tissue culture media such as, for example, Basal Medium Eagle's (BME), Eagle's Minimum Essential Medium (MED), Dulbecco's Modified Eagle Medium, Medium 199 and balanced salt solutions (BSS) such as those of Earle and Hanks fortified with various nutrients. These are commercially available tissue culture media and are described in detail by H. J. Morton *In Vitro* 6, 89–108 (1970). These culture media contain known essential amino acids, mineral salts, vitamins and carbohydrates. They are also frequently fortified with mammalian sera such as fetal calf serum.

Prior to the suspension culturing, the established cell line should be grown in the desired culture medium to a stage beyond that of ordinary monolayer growth in a substrate-attached culture whereby multilayers of cells are produced and cell-to-cell contacts are established in three dimensions. This can be accomplished by frequent reseedings of the substrate-attached cells without subcultivation. This growth can be carried out in ordinary culture flasks such as Falcon 75 cm² flasks.

The treatment employed for release of the cells from the substrate is critical. It must be such as to produce aggregates or clumps of cells ranging from abut 20 $\mu$ to about 500 $\mu$ in diameter. Within this range, it is preferred that about 75% of the cells are in aggregates of from about six to about 100 cells per aggregate. It will be appreciated that a small proportion of single cells may be present due to their failure to clump together or as a result of their separation from the cell aggregates during handling of the cells. It is preferred to avoid transferring an undue number of such single cells to the agitated liquid suspension culture since they tend to die. When the cell aggregates are too large, such as greater than about 500 $\mu$ in diameter, insufficient nutrients reach those cells in the center, and toxic materials are elaborated which inhibit growth or destroy the viability of the cells.

The desired release of the cells from the substrate is facilitated by enzymatic dissociation such as trypsinization and the like at room temperature (generally about 20°–25° C) accompanied by careful observation under a microscope. The enzymatic treatment can result in three different physical arrangements of cells, namely, as single cells, as aggregates or clumps of cells, or as large cell sheets. When the cells are released in aggregates of the desired size, no further treatment is necessary. However, if the cells are released predominantly singly or in large sheets, further action must be taken. When released singly, the culture flasks are allowed to stand at room temperature until the desired clumps form. The cells released by the enzymatic treatment are sticky and will form aggregates after a period of time if not agitated. When large cellular sheets are formed, these should be subdivided or broken into the desired aggregate size by gentle agitation such as shaking or by passage through a small orifice such as a pipet tip or needle having the desired diameter.

Enzymes suitable for use in the foregoing release of cells from the substrates are by way of example and not limitation, trypsin, pronase, collagenase and hyaluronidase. Trypsin is the preferred enzyme and is readily available commercially from enzyme houses such as Miles Laboratories, Inc. and Worthington Biochemical Corp. For background information on the use of these enzymes in primary tissue dissociation, reference can be had to Kruse and Patterson, "Tissue Culture Methods and Applications", Academic Press, 1973, at Section 1, pp. 3–36.

After appropriate release from the substrate, the cell aggregates are transferred into a rapidly stirred spinner vessel containing fresh culture medium. These vessels can be made, for example, of a glass, plastic or metal construction. A stainless steel jacketed fermenter of the type manufactured by the New Brunswich Scientific Co., Inc. is generally suitable upon being modified to remove the baffles as are glass spinner bottles of the type manufactured by Bellco Glass Inc. Illustrative of such fermentors are the devices described in U.S. Pat Nos. 3,445,341 and 3,445,342. Examples of the stirred spinner bottles are those disclosed in U.S. Pat. Nos. 2,958,517 and 3,622,129. Another such apparatus for agitated liquid suspension culturing on a large scale is described in U.S. Pat. No. 3,039,932. The stirring speed in the use of these spinner vessels preferably should range from about 200 to about 300 r.p.m.

In order to ensure satisfactory propagation of cells in the suspension culture, the concentration of cells transferred from the attached substrate to the spinner vessel should be at least about $10^6$ cells/ml of suspension.

During the suspension culturing, the pH should be maintained at about 6.7 to about 7.7 and preferably at about 7.0 to about 7.4. This pH can be appropriately maintained by use of a suitable buffer such as, for example, phosphate buffered saline (PBS) or other well known buffers having the stated pH.

The culture temperature should range from about 30° C to about 38° C and preferably from about 35° C to about 37° C.

During the suspension culture growth period, successive transfers of the growing cells into fresh media can be made at predetermined periodic intervals. These transfers can be made into increasingly larger size culture vessels containing fresh nutrient media as before in order to facilitate the rapid proliferation of cells on a large scale.

Following suitable cell growth, for example, after a two-week cell culturing period at 35° C to 37° C, the cells can be harvested from the suspension such as be sedimentation or centrifugation at 200–1000 g. The packed cells are then thoroughly washed such as in saline solution, lactated Ringer's solution, PBS and other such aqueous solutions, having a pH of from about 6.7 to about 7.7 and preferably from about 7.0 to about 7.4. The washed cells can be retained for further use as needed or extracted for desired products, such as enzymes, hormones, antibodies and cell metabolites.

The following detailed examples will further illustrate the invention although it will be appreciated that the invention is not limited to these specific examples.

EXAMPLE 1

A culture of the human lung, SV-40 transformed cell line designated WI25, VA4, was obtained from the American Type Culture Collection under the deposit number CCL 95.1. The culture was maintained for 60 days, substrate attached, in 75 cm² plastic Falcon flasks. During this period, the cells were adapted to the medium to be used for the subsequent suspension culture, namely, Dulbecco's Modified Minimum Essential Medium with 4.5 g/ml glucose and supplemented with 10% fetal calf serum. The cells were subcultured at weekly intervals and the medium was charged with fresh medium every two days. During the last two weeks, the cells were not subcultivated, but were maintained with daily medium replenishment.

After the 60 day period, six 75 cm² flasks of densely packed, multilayered cells were harvested as follows:

The expended medium was poured off. Phosphate buffered saline (PBS) at pH 7.2 with 0.02% disodium ethylenediamine tetraacetate (EDTA) was used to rinse the attached cells. The rinsing was repeated. Then 5 ml. of 0.2% trypsin in PBS with 0.02% EDTA was added and allowed to stand over the cells at room temperature. The flasks were carefully observed on an inverted microscope. After three minutes of standing, slight agitation of the flasks produced cell aggregates in the desired range of 20 $\mu$ to 500 $\mu$ diameter. This agitation was produced by holding the flask upright in one hand with cells attached to the surface below the liquid and gently striking into the palm of other hand. Motion was thus caused which ranged from slight waves to turbulent washing of cells in the liquid. The cells thereby experienced a shearing force between moving liquid and the relatively stationary flask.

The resulting 5 ml. cell aggregate suspension was transferred to a 500 ml Bellco spinner flask containing 200 ml of medium. The culture was incubated in a warm room at 37° C with a stirring rate of about 250 r.p.m. The cells continued to grow with no observed decrease or lag in rate. Medium was added at periodic intervals and the culture was transferred to larger vessels as follows:

After 48 hours, additional medium was added to bring the total suspension volume to 500 ml.

After a total of 144 hours, 400 ml. of suspension was used to inoculate a 3 liter Bellco spinner vessel containing 2 liters of medium. Four hundred ml. of fresh medium was added to the original 500 ml. spinner bottle. The 3 liter spinner bottle was overlayed with one liter per minute of 5% $CO_2$ in air. Both bottles continued to be stirred at 250 rpm in the 37° C warm room.

The volume of suspension in the 3 liter spinner bottle was increased to 4 liters (one liter above the rated capacity) with fresh medium after a total of 240 hours of aggregate suspension culture. The 500 ml. spinner bottle was harvested and the cells were frozen in liquid nitrogen at this time.

At 335 hours, three liters of suspension were transferred to a 12 liter spinner vessel and fresh medium was added to the 3 liter and 12 liter spinner bottles to bring their volumes to 4 and 12 liters, respectively. Both were incubated with 5% $CO_2$ in air overlay at 37° C and 250 rpm.

After a total of 480 hours since initiation of aggregate suspension culture, the 16 liters of suspension was harvested by centrifugation to yield 30 ml of packed cells. DNA determination (140±2.6 mg DNA) indicated a yield of about $1.4 \pm 0.03 \times 10^{10}$ cells.

EXAMPLE 2

Another normally anchorage-dependent human cell line, the human lung, SV-40 transformed cell line designated WI38, VA13 (ATCC No. CCL 75.1), was rapidly adapted to agitated liquid suspension culture under substantially the same procedures and conditions used in Example 1. After a total of 38 days since initiation of aggregate suspension culture, 16 liters of suspension was harvested to yield $1.84 \pm 0.3 \times 10^{10}$ cells.

EXAMPLE 3

A third normally anchorage-dependent cell line, the mouse kidney, SV-40 transformed cell line designated TCMK-1 (ATCC No. CCL 139), was rapidly adapted to agitated liquid suspension culture under substantially the same procedures and conditions used in Example 1. After a total of 19 days since initiation of aggregate suspension culture, 16 liters of suspension was harvested to yield $2.57 \pm 0.05 \times 10^{10}$ cells.

EXAMPLE 4

Another normally anchorage-dependent mouse cell line, the mouse embryo, SV-40 transformed cell line designated SV3T3, was rapidly adapted to agitated liquid suspension culture under substantially the same procedures and conditions used in Example 1. After a total of 14 days since initiation of aggregate suspension culture, 60 liters of suspension was harvested to yield $8.1 \pm 0.22 \times 10^{10}$ cells.

EXAMPLE 5

Another normally anchorage-dependent mouse embryo cell line, the Kirsten virus transformed cell line designated KNIH, was rapidly adapted to agitated liquid suspension culture under substantially the same procedures and conditions used in Example 1. After a total of 15 days since initiation of aggregate suspension culture, 60 liters of suspension was harvested to yield a visually observed significant quantity of cells, although an actual cell count was not determined as in Example 1.

EXAMPLE 6

Still another normally anchorage-dependent mouse cell line, the mouse renal adenocarcinoma cell line designated RAG(ATTCC No. CCL 142), was rapidly adapted to agitated liquid suspension culture under substantially the same procedures and conditions used in Example 1. After a total of 10 days since initiation of aggregate suspension culture, 4 liters of suspension was harvested to yield a visually observed significant quantity of cells, although an actual cell count was not determined as in Exmple 1.

Various other examples will be apparent to the person skilled in the art after reading the disclosure herein without departing from the spirit and scope of the invention and it is intended that all such further examples be included within the scope of the appended claims.

What is claimed is:

1. A method of rapidly adapting normally anchorage-dependent established cell lines to agitated liquid suspension culture comprising growing an inoculum of said cell line in substrate-attached culture to a stage beyond that of ordinary monolayer growth whereby multilayers of cells are produced, releasing the cells from the substrate-attached culture in the form of cell aggregates ranging from about 20 microns to about 500 microns in diameter, transferring said aggregates into a liquid suspension of nutrient culture medium of known essential amino acids, mineral salts, vitamins and carbohydrates, incubating at a temperature of from about 30° C to about 38° C while substantially continuously maintaining agitation of said medium, periodically transferring the growing cells into fresh nutrient medium and continuing the agitated incubation whereby said cells continue to be proliferated in aggregates.

2. The method of claim 1 on which the incubation temperature is from about 35° C to about 37° C.

3. The method of claim 1 in which two periodic transfers of the growing cells into fresh nutrient culture medium are made at predetermined intervals.

4. The method of claim 1 in which the nutrient culture medium is fortified with mammalian serum.

5. The method of claim 1 in which the cell line is an SV-40 transformed cell line.

6. The method of claim 1 in which the nutrient culture medium is Dulbecco's Modified Minimum Essential medium.

7. The method of claim 1 in which the releasing of the cells from the substrate-attached culture is facilitated by dissociation with enzymes.

8. The method of claim 7 in which the enzyme is trypsin.

9. The method of claim 7 in which the dissociation with enzyme is accompanied by gentle agitation.

10. The method of claim 9 in which the enzyme is trypsin.

11. The method of claim 7 in which the releasing of the cells from the substrate-attached culture is further accompanied by careful observation with the aid of a microscope to ensure the formation of cell aggregates in said range of diameter.

12. The method of claim 9 in which the releasing of the cells from the substrate-attached culture is further accompanied by careful observation with the aid of a microscope to ensure the formation of cell aggregates in said range of diameter.

* * * * *

UNITED STATES PATENT AND TRADEMARK OFFICE
CERTIFICATE OF CORRECTION

PATENT NO. : 4,059,485
DATED : November 22, 1977
INVENTOR(S) : William R. Tolbert and Joseph Feder It is certified that error appears in the above-identified patent and that said Letters Patent are hereby corrected as shown below:

In Column 3, line 2, "MED" should be --MEM--.

In Column 4, line 56 (Example 1) the cell line identified as "WI25" should be --WI26--.

Signed and Sealed this

Ninth Day of October 1979

[SEAL]

Attest:

RUTH C. MASON
Attesting Officer

LUTRELLE F. PARKER
Acting Commissioner of Patents and Trademarks